United States Patent [19]

Williams et al.

[11] 4,031,103
[45] June 21, 1977

[54] 1,8-NAPHTHYRIDINE COMPOUNDS

[75] Inventors: Hayden Windsor Richard Williams, Dollard des Ormeaux; Clarence Stanley Rooney, Beaconsfield, both of Canada

[73] Assignee: Merck Sharp & Dohme (I.A.) Corporation, Rahway, N.J.

[22] Filed: Dec. 9, 1975

[21] Appl. No.: 639,036

Related U.S. Application Data

[62] Division of Ser. No. 477,392, June 7, 1974, Pat. No. 3,962,262, which is a division of Ser. No. 350,285, April 11, 1973, Pat. No. 3,843,663.

[52] U.S. Cl. .................. 260/295 N; 260/294.8 C; 260/296 N; 424/263
[51] Int. Cl.[2] ....................................... C07D 213/44
[58] Field of Search ........ 260/296 N, 297 Z, 297 R, 260/295 N

[56] References Cited

UNITED STATES PATENTS

| | | | |
|---|---|---|---|
| 1,755,515 | 4/1930 | Rath ........................... | 260/296 N |
| 2,226,111 | 12/1940 | Binz et al. .................... | 260/296 N |
| 2,517,929 | 8/1950 | Richter ........................ | 260/296 N |
| 3,842,087 | 10/1974 | Williams et al. ............... | 260/295 N |
| 3,843,663 | 10/1974 | Williams et al. ............... | 260/296 N |
| 3,962,262 | 6/1976 | Williams et al. ............. | 260/294.8 C |

OTHER PUBLICATIONS

Ochiai et al., Ber. Deut. Chem., vol. 74, pp. 1115 to 1126 (1941).
Elderfield, Heterocyclic Compounds, vol. 7, front page and pp. 206–207 and 232, John Wiley and Sons, Inc. (1961).

*Primary Examiner* — John D. Randolph
*Attorney, Agent, or Firm* — Edmunde D. Riedl; Julian S. Levitt; David L. Rose

[57] ABSTRACT

There is described 2-amino-5,7-disubstituted-naphthyridine and 5,7-disubstituted-naphthyridin-2(1H)-one derivatives with bronchodilating and hypotensive properties prepared by the reaction of 2,6-diaminopyridine with an appropriate $\beta$-diketone providing the 2-amino products. The 2-oxo analogs are prepared from the 2-amino products by treatment with nitrous acid.

3 Claims, No Drawings

1,8-NAPHTHYRIDINE COMPOUNDS

This is a division of application Ser. No. 477,392 filed June 7, 1974, now U.S. Pat. No. 3,962,262 granted June 8, 1976, which in turn was a division of Ser. No. 350,285 filed Apr. 11, 1973 now U.S. Pat. No. 3,843,663 granted on Oct. 22, 1974.

This invention is concerned with 2-amino-5,7-disubstituted-1,8-naphthyridine and 5,7-disubstituted-naphthyridin-2(1H)-one compounds and processes for their preparation.

The novel compounds of this invention have one of the general structural formulae I or II

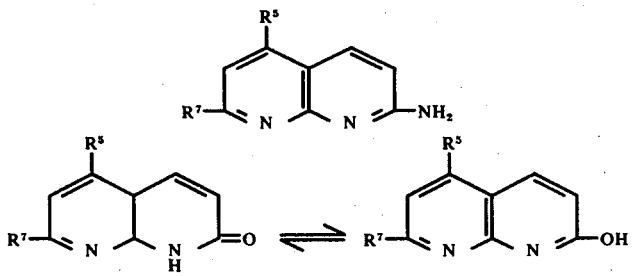

wherein $R^5$ is selected from lower alkyl having from 1 to 5 carbon atoms, halo substituted lower alkyl, preferably trifluoromethyl and pentafluoroethyl, phenyl, pyridyl, thienyl and naphthyl, $R^7$ is selected from lower alkyl having from 1 to 5 carbon atoms and halo-substituted lower alkyl, preferably trifluoromethyl and pentafluoroethyl, and one or both of the variable radicals $R^5$ and/or $R^7$ is a haloalkyl.

The 2-oxo products (II) are keto-enol tautomers. However as the keto form is considered the more stable tautomer, the products herein will be named as 2-oxo compounds although those skilled in the art will realize that both tautomers may be present or any particular compound so named may exist as the enol or hydroxy tautomer and the following disclosure therefore is to be interpreted to incorporate all tautomeric forms.

The naphthyridine compounds of this invention have been shown to increase the concentration of 3',5'-cyclic adenosine monophosphate in vitro and have been found in animal studies to inhibit bronchial constriction induced by histamine and other constricting agents and are therefore useful as bronchodilating agents. As bronchodilating agents, the products of this invention have been found to have relatively low chronotropic effect as compared with known bronchial dilator agents. Additionally the products possess useful hypotensive properties.

The process aspect of our invention resides in the reaction of 2,6-diaminopyridine with the appropriate β-diketone to provide the 2-amino-5,7-disubstituted-1,8-naphthyridine compounds. The reaction is facilitated by warming up to the boiling point although in practice lower temperatures, up to 90°-95° C., have been found to provide operable conditions. When $R^5$ and $R^7$ represent dissimilar substituents, the reaction sometimes forms both isomers. When two isomers are obtained they can readily be separated by conventional methods, conveniently by chromatographic separation on silica gel using ethyl acetate, methanolbenzene, acetone, as well as other known developing solvents.

The 2-oxo compounds are obtained by treatment of the 2-amino compound with nitrous acid. The prior art procedure for converting 2amino-1,8-naphthyridine compounds to the corresponding 2-oxo compound using dilute sulfuric acid and sodium nitrite was found to be inoperative for the compounds of this invention having a haloalkyl substituent attached to the naphthyridine nucleus. It was discovered, however, that for all of the products of this invention conversion of the 2-amino to the 2-oxo group could be effected by use of trifluoroacetic acid or pentafluoropropionic acid and an alkali metal nitrite, suitably sodium or potassium nitrite which provides the 2-oxo analog in good yield. Conversion takes place readily at ambient temperature. Slight warming would not, however, be contraindicated.

The process for making the novel compounds of this invention can be illustrated schematically as follows:

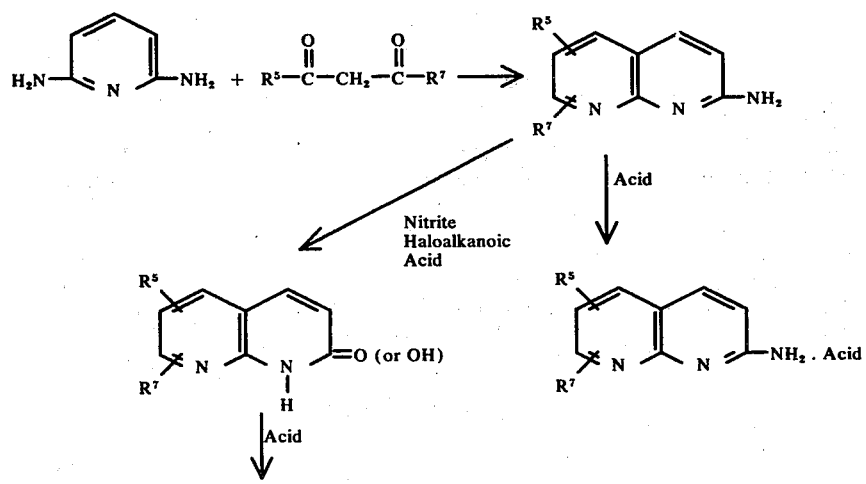

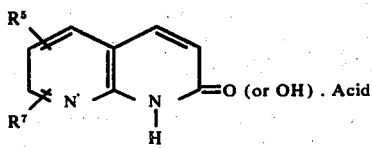

The following examples will provide details of the reaction conditions employed in preparing the compounds as well as illustrate the preparation of certain compounds falling within the scope of this invention.

EXAMPLE 1

2-Amino-5,7-di(trifluoromethyl)-1,8-naphthyridine

A mixture of 2,6-diaminopyridine (5.2 g., 47.6 mmole), 1,1,1,5,5,5-hexafluoroacetylacetone (10.0 g., 48.0 mmole) and 85% phosphoric acid (50 ml.) are stirred for six hours in an oil-bath at 90°–95° C. then left overnight at ambient temperature. The reaction mixture is poured into ice water and neutralized with ammonium hydroxide to pH 7, the solid collected, washed with water and dried to provide 9.0 g. (67%) of product, m.p. 198–204° C. Upon recrystallization from benzene, purified product separates in the form of pale yellow needles, m.p. 204°–206° C.

Analysis calculated for $C_{10}H_5F_6N_3$: C, 42.72; H, 1.79; F, 40.54; N, 14.94; Found: C, 42.77; H, 2.13; F, 40.33; N, 15.23.

EXAMPLE 2

2-Amino-5-methyl-7-trifluoromethyl-1,8-naphthridine
and
2-Amino-5-trifluoromethyl-7-methyl-1,8-naphthyridine By replacing the hexafluoroacetylacetone employed in Example 1 by an equivalent quantity of 1,1,1,-trifluoroacetylacetone and following substantially the same procedure described in Example 1, there is obtained a mixture of the two products which are isolated from the crude reaction mixture by chromatographic separation of silica gel using ethyl acetate as the developing agent. There is thus obtained a 17.6% yield of 2-amino-5-methyl-7-trifluoromethyl-1,8-naphthyridine which melts at 255°–257° C. following purification by recrystallization from toluene.

Analysis calculated for $C_{10}H_8F_3N_3$: C, 52.87; H, 3.55; F, 18.50; N, 25.08; Found: C, 52.69; H, 3.75; F, 18.77; N, 25.41;
and a 20.6% yield of 2-amino-5-trifluoromethyl-7-methyl-1,8-naphthyridine which melts at 195°–197° C. (dec.) following recrystallization from benzene.

Analysis Found: C, 52.99, H, 3.75, F, 18.79, F, 25.18.

EXAMPLE 3

2-Amino-5-(2-thienyl-7-trifluoromethyl-1,8-naphthyridine

By replacing the hexafluoroacetylacetone employed in Example 1 by an equivalent quantity of 1-trifluoromethyl-5-(2-thienyl)-propane-1,3-dione and following substantially the same procedure described in Example 1 there is obtained a 15.3% of yield of product which melts at 256°–258° C. after recrystallization from ethyl acetate.

Analysis calculated for $C_{13}H_{10}F_3N_3S$: C, 52.88; H, 2.73; N, 14.23; F, 19.30; Found: C, 53.39; H, 2.84; N, 13,87; F, 19.26; C, 53.09; -thienyl)-propane-2.95; N, 14.43; F, 19.24.

EXAMPLE 4

5,7Di(trifluoromethyl)-1,8-naphthyridine-2(1H)-one

2-Amino-5,7-ditrifluoromethyl-1,8-naphthyridine, prepared as described in Example 1, (5.60 g., 20 mmoles) is dissolved in trifluoracetic acid (40 ml.). To the stirred, cooled (ice bath), solution is added finely powdered sodium nitrite (3.0 g., 43.5 mmoles) in small portions. Stirring is continued at room temperature for one hour, the mixture then poured into a crushed ice/water mixture (ca. 500 ml.), and the product filtered off and dried in an oven at 60° C. yielding 4.2 g. (75%) of crude product. Following purification by recrystallization from isopropyl ether there is obtained 3.4 g. (60%) of pure product, m.p. 182°–184° C.

Analysis calculated for $C_{10}H_4F_6N_2O$: C, 42.57; H, 1.43; F, 40.40; N, 9.92; Found: C, 43.02; H, 1.66; F, 40.25; N, 10.22.

By following the procedure of Example 4 but replacing the 2-amino-5,7-di(trifluoromethyl)-1,8-naphthyridine by an equivalent quantity of the products of Examples 2 and 3, respectively, that is by employing 2-amino-5-methyl-7-trifluoromethyl-1,8-naphthyridine
2-amino-5-trifluoromethyl-7-methyl-1,8-naphthyridine
2-amino-5-(2-thienyl)-7-trifluoromethyl-1,8-naphthyridine
there is obtained, respectively.

EXAMPLE 5

5-Methyl-7-trifluoromethyl-1,8-naphthyridin-2(1H)-one,

69% yield, m.p. 200°–202° C.

Analysis calculated for $C_{10}H_7F_3N_2O$: C, 52.64; H, 3.09; F, 24.97; N. 12.27; Found: C, 52.39; H, 3.52; F, 25.10; N, 12.36.

EXAMPLE 6

5-Trifluoromethyl-7-naphthyl-1,8-naphthyridin-2(1H)-one,

35% yield, m.p. 169°–167° C. following recrystallization from ethyl acetate.

Analysis calculated for $C_{10}H_7F_3N_2O$: C, 52.64; H, 3.09; F, 24.97; N, 12.27; Found: C, 52.70; H, 3.21; F, 25.32; N, 12.47.

EXAMPLE 7

5-(2-Thienyl)-7-trifluoromethyl-1,8-naphthyridin-2(1H)-one,

12% yield, m.p. 103° C. following recrystallization from ethyl acetate.

Analysis calculated for $C_{13}H_7F_3N_2OS$: C, 52.70; H, 2.38; F, 19.23; N, 9.45; S, 10.82; Found: C, 53.17; H, 2.15; F, 19.41; N, 9.35; S, 11.08.

The products identified in Table I are prepared by the methods described in Examples 1 and 4. The 2-amino products having the substituents 5- and 7- are prepared by replacing the 1,1,1,5,5,5-hexafluoroacetylacetone employed in Example 1 by an equivalent quantity of the β-diketone identified in the table. When a mixture of isomers is obtained they are separated by known chromatographic methods such as described herein and illustrated in Example 2. The 2-oxo analog of each product is obtained by nitrozation of the amino group as described in Example 4.

TABLE I

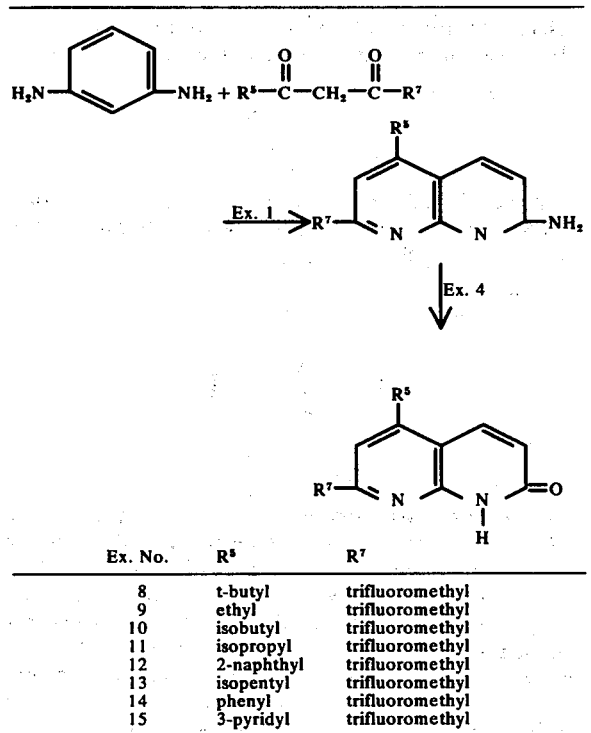

| Ex. No. | R⁵ | R⁷ |
|---|---|---|
| 8 | t-butyl | trifluoromethyl |
| 9 | ethyl | trifluoromethyl |
| 10 | isobutyl | trifluoromethyl |
| 11 | isopropyl | trifluoromethyl |
| 12 | 2-naphthyl | trifluoromethyl |
| 13 | isopentyl | trifluoromethyl |
| 14 | phenyl | trifluoromethyl |
| 15 | 3-pyridyl | trifluoromethyl |

EXAMPLE 16

2-Amino-5,7-di(pentafluoroethyl)-1,8-naphthyridine

STEP A

Preparation of 1,1,1,2,2,6,6,7,,7,7-Decafluoroheptan-3,5-dione

To a stirred suspension of potassium t-butoxide (44.5 g., 0.4 mole) in dry ether (400 ml.) is added ethyl pentafluoropropionate (76.8 g., 0.4 mole) over a period of about 15 minutes. Most of the solid dissolves. A solution of pentafluoroethyl methyl ketone (64.8 g., 0.4 mole) in dry ether (60 ml.) is added slowly, and after stirring the mixture for 2 hours at room temperature, it is allowed to stand overnight. A solution of glacial acetic acid (27.2 ml.) in water (120 ml.) is added with stirring and external cooling (ice-bath). Then a warm solution of copper acetate (56.0 g., 0.23 mole) in water (532 ml.) is added slowly with stirring and cooling. The ether is distilled off, and the copper salt of the product is collected by filtration, washed with water, drained thoroughly, and then washed with petroleum ether. The copper derivative is suspended in ether (200 ml.) and decomposed by treatment with 15% sulphuric acid (450 ml.). The aqueous layer is separated and extracted with more ether (3 × 50 ml.). The combined ethereal extract is dried, first over anhydrous sodium sulphate and then over anhydrous calcium sulphate. Evaporation of the ether gives the product which is purified by fractionational distillation at atmospheric pressure.

STEP B

Preparation of 2-Amino-5,7-di(pentafluoroethyl)-1,8-naphthyridine

A mixture of 2,6-diamino pyridine (5.2 g., 4.76 mmole), 1,1,1,2,2,6,6,7,7,7-decafluoroheptan-3,5-dione (14.5 g., 4.80 mmole) and 85% phosphoric acid (50 ml.) is stirred at 90°–95° C. for 6 hours. When cool, the reaction mixture is poured into ice-water and neutralized with ammonium hydroxide to pH 7. The solid is collected, washed with water, dried, and can be purified by recrystallization from benzene.

EXAMPLE 17

2-Amino-5-methyl-7-pentafluoroethyl-1,8-naphthyridine and 2-Amino-7-methyl-5-pentafluoroethyl-1,8-naphthyridine When the decafluoroheptanedione in the foregoing example is replaced by 1,1,1,2,2-pentafluorohexan-3,5-dione (9.80 g., 4.80 mmole), the crude product is a mixture of two isomeric naphthyridines. The two compounds, 2-amino-5-methyl-7-pentafluoroethyl-1,8-naphthyridine and 2-amino-7-methyl-5-pentafluoroethyl-1,8-naphthyridine, are separated by chromatography on silica gel using ethyl acetate or carbon tetrachloride/chloroform as the solvent phase, and purified by recrystallizing the separated fractions from benzene.

EXAMPLE 18

5-Methyl-7-pentafluoroethyl-1,8-naphthyridin-2(1H)-one

2-Amino-5-methyl-7-pentafluoroethyl-1,8-naphthyridine (5.54 g., 20 mmole) is dissolved in trifluoroacetic acid (40 ml.) and to the stirred solution cooled to −5° to 0° C. is added finely powdered sodium nitrite (3.0 g., 43.5 mmole) in small portions. Stirring of the mixture is continued at room temperature for one hour, after which it is poured into ice-water (ca. 500 ml.). The product precipitates and is collected, washed and dried at 60° C. in air. It can be purified by recrystallization from diisopropyl ether.

Example 19

7-Methyl-5-pentafluoroethyl-1,8-naphthyridin-2(1H)-one

7-Methyl-5-pentafluoromethyl-1,8-naphthyridin-2(1H)-one is obtained in a similar way, when 2-amino-7-methyl-5-pentafluoroethyl-1,8-naphthyridine is substituted for 2-amino-5-methyl-7-pentafluoroethyl-1,8-naphthyridine in the foregoing example.

EXAMPLE 20

5,7-Di(pentafluoroethyl)-1,8-naphthyridin-2-(1H)-one

When an equivalent amount (7.62 g., 20 mmole) of 2-amino-5,7-di(pentafluoroethyl)-1,8-naphthyridine is used in place of the 2-amino-5-methyl-7-pentafluoroethyl-1,8-naphthyridine employed in Example 18, the product is 5,7-di(pentafluoroethyl)-1,8-naphthyridin-2(1H)-one. Purification is effected by recrystallization of the crude product from a mixture of benzene and petroleum ether.

The products of this invention were found, when tested according to standard protocols in anesthetized dogs to inhibit bronchial constriction induced by one or more bronchoconstricting agents; a known procedure for evaluating the bronchodilating properties of products. In addition, the compounds were also found to exhibit hypotensive properties, probably due to their action as peripheral vasodilators and are therefore potentially useful for the treatment of hypertension. Intravenous or intraduodenal doses in the approximate dose range of 5 mg./kg. to 75 mg./kg. provided protection at the $ED_{50}$ level against the induced bronchoconstriction in most animals challenged. Those compounds that also exhibited hypotensive properties were effective within the same dosage range.

The invention further provides pharmaceutical compositions comprising, as active ingredient, at least one of the compounds according to the invention in association with a pharmaceutical carrier or excipient to which other active ingredients can be added, if desired. The product or products may be presented in a form suitable for application orally (such as capsules, tablets or liquid preparations), or for parenteral administration (in the form of solutions or suspensions) or in aerosols prepared by conventional methods. For example, a capsule can be prepared by conventional methods employing lactose as an excipient and containing per unit dosage 10–25 mgs. of active compound. Unit dosages can range between about 5 to 100 mg. for adminstration as prescribed by the physician.

While the invention has been illustrated by certain specific members of the novel 1,8-naphthyridine products made by certain specific methods and formulated into certain specific dosage forms, it is to be understood that the invention is not to be considered limited by or to the specific embodiments illustrated but is to encompass other members of the novel products falling within the scope of the generic disclosure and claims as well as other methods or modifications of the methods described for their preparation and other formulations, all of which would be obvious in view of the teaching herein to one skilled in the art.

We claim:

1. A process for the preparation of a 1,8-naphthyridine compound having the structures

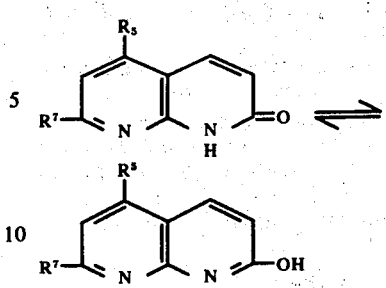

which comprises admixing equimolar quantities of 2,6-diaminopyridine and a β-diketone of the structure

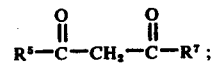

warming the admixture to its boiling point to initiate reaction providing a 2-amino-1,8-naphthyridine compound having the structure

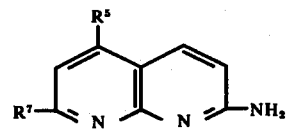

I and, reacting said 2-amino-1,8-naphthyridine with an alkali metal nitrite in the presence of trifluoroacetic acid or pentafluoropropionic acid wherein, in each of the foregoing structures $R^5$ is selected from the group consisting of lower alkyl, trifluoromethyl, pentafluoroethyl, phenyl, pyridyl, thienyl and naphthyl; $R^7$ is selected from the group consisting of lower alkyl, trifluoromethyl and pentafluoroethyl, and at least one of $R^5$ or $R^7$ is trifluoromethyl or pentafluoroethyl.

2. A process as claimed in claim 1 wherein 2,6-diaminopyridine is reacted with 1,1,1,5,5,5-hexafluoroacetylacetone to provide 2-amino-5,7-di(trifluoromethyl)-1,8-naphthyridine.

3. A process as claimed in claim 1 wherein 2,6-diaminopyridine is reacted with 1,1,1-trifluoroacetylacetone and the 2amino-5-methyl-7-trifluoromethyl-1,8-naphthyridine and 2-amino-5-trifluoromethyl-7-methyl-1,8-naphthyridine thus obtained converted to the 2-oxo analogs by reaction with an alkali metal nitrite in the presence of trifluoroacetic acid or pentafluoropropionic acid to provide 5-methyl-7-trifluoromethyl-1,8-naphthyridin-2(1H)-one and 5-trifluoromethyl-7-methyl-1,8-naphthyridin-2(1H)-one.

* * * * *